United States Patent [19]

Kondo et al.

[11] Patent Number: 4,675,662

[45] Date of Patent: Jun. 23, 1987

[54] MACHINE OIL DETERIORATION DETECTION

[75] Inventors: Kenji Kondo, Aichi; Tadashi Hattori, Okazaki; Kinya Atsumi, Toyohashi; Minoru Nishida, Okazaki, all of Japan

[73] Assignee: Nippon Soken, Inc., Nishio, Japan

[21] Appl. No.: 761,416

[22] Filed: Aug. 1, 1985

[30] Foreign Application Priority Data

Aug. 6, 1984 [JP] Japan .................... 59-163883
May 6, 1985 [JP] Japan .................... 60-96231

[51] Int. Cl.[4] ............................ G08B 21/00
[52] U.S. Cl. ...................... 340/631; 324/65 P; 340/59; 340/603; 340/604; 340/620
[58] Field of Search ............ 340/631, 620, 604, 603, 340/602, 59; 73/304 R; 324/65 P, 65 R; 338/27, 28

[56] References Cited

FOREIGN PATENT DOCUMENTS 59-88207  6/1984  Japan .
59-91408  6/1984  Japan .

Primary Examiner—James L. Rowland
Assistant Examiner—Daniel Myer
Attorney, Agent, or Firm—Cushman, Darby & Cushman

[57] ABSTRACT

A machine oil deterioration detection apparatus having a copper thin film resistor formed on an electrically insulating holding member and immersed in a machine oil. The copper thin film resistor is corroded by acid produced in accordance with deterioration of the machine oil, thus changing the resistance of the resistor. The change in resistance is detected by a detection circuit, connected to the thin film resistor, for detecting the resistance of the thin film resistor.

5 Claims, 12 Drawing Figures

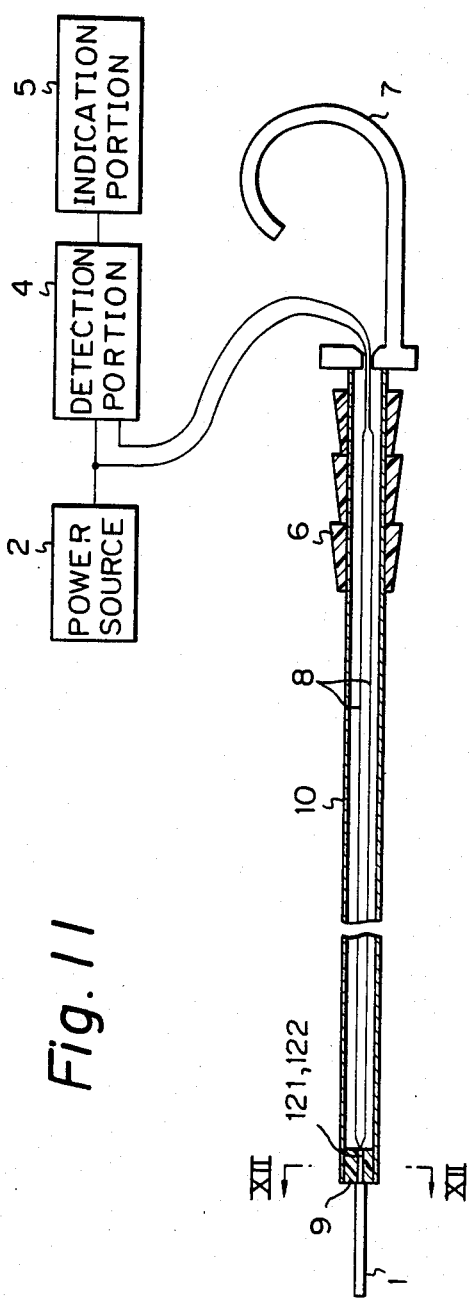
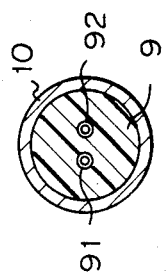
Fig. 11
Fig. 12

MACHINE OIL DETERIORATION DETECTION

BACKGROUND OF THE INVENTION

1. Field of the Invention

The present invention relates to an apparatus for detecting the degree of deterioration of a machine oil, e.g., the engine oil of a vehicle.

2. Description of the Related Art

In a conventional apparatus for detecting deterioration of the engine oil of a vehicle, a metal lead wire is used as an oil deterioration sensor. This metal lead wire is corroded by an acidic substance produced due to deterioration of the oil, and thus the resistance of the wire is increased or the wire is eventually disconnected.

However, in the conventional apparatus, the texture of the metal lead wire is dense, the rate of corrosion by the acidic substance is low, and the wire is corroded only on the order of angstroms. Thus, to precisely detect deterioration of the oil, a very thin metal lead wire must be used. Accordingly, when electrodes are connected directly to two ends of such a very thin metal lead wire, the mechanical strength of the wire cannot be guaranteed. In particular, in a vehicle subjected to continuous external vibration, and in which the pressure of the oil in the oil pan is increased under a high engine load, the metal lead wire may become disconnected even though the oil is not deteriorated, resulting in an erroneous detection signal.

In the conventional apparatus, an iron (Fe) wire is used as the metal lead wire. However, after extensive research, the present inventors have found that an iron wire does not exhibit a linear change in resistance with respect to oil deterioration. That is, according to their research, the present inventors have found that the surface of an iron wire was corroded by acid in the oil immediately after the wire was dipped in the oil, changing the resistance of the wire. However, thereafter, a very thin passive film of a carbonyl group was formed on the surface of the iron wire due to chemical reaction, and the iron wire could no longer be corroded.

Thus, although an apparatus has been proposed wherein a metal lead wire dipped into oil is used as an oil deterioration sensor, an optimum material and structure have not been found, and this has caused a critical problem in practice. The above conventional machine oil deterioration detection apparatus is described in, e.g., *Japanese Unexamined Utility Model Publications (Kokai)* Nos. 59-91408 and 59-88207.

SUMMARY OF THE INVENTION

It is, therefore, an object of the present invention to provide an improved machine oil deterioration detection apparatus having a high detection precision and reliability when deterioration of a machine oil is detected by a change in resistance of a metal conductor immersed in the machine oil.

It is another object of the present invention to provide an improved machine oil deterioration detection apparatus which uses a metal resistor corroded only by an acidic substance produced in accordance with deterioration of the oil without being disconnected due to external vibration or oil pressure.

According to the present invention, there is provided an apparatus for detecting the degree of deterioration of machine oil, including: a thin film resistor member of copper formed on an electrically insulating holding member and dipped in the machine oil, the thin film resistor member being corroded to change the resistance thereof by an acid produced due to deterioration of the machine oil; electrode members conductively provided at two ends of the thin film resistor member on the electrically insulating holding member; and a resistance detection circuit connected to the electrode members for detecting a change in resistance of the thin film resistor member.

BRIEF DESCRIPTION OF THE DRAWINGS

FIGS. 9 and 10 show an arrangement in which an insulating film is formed on a connecting portion of a thin film resistor and an electrode member, in which FIG. 10 is a sectional view taken along a line X—X of FIG. 9; and FIGS. 11 and 12 show an arrangement in which the machine oil deterioration detection element is mounted on an oil level gauge (dipstick) in a vehicle engine, in which FIG. 12 is a sectional view taken along a line XII—XII of FIG. 11.

DESCRIPTION OF THE PREFERRED EMBODIMENTS

Figure 1:
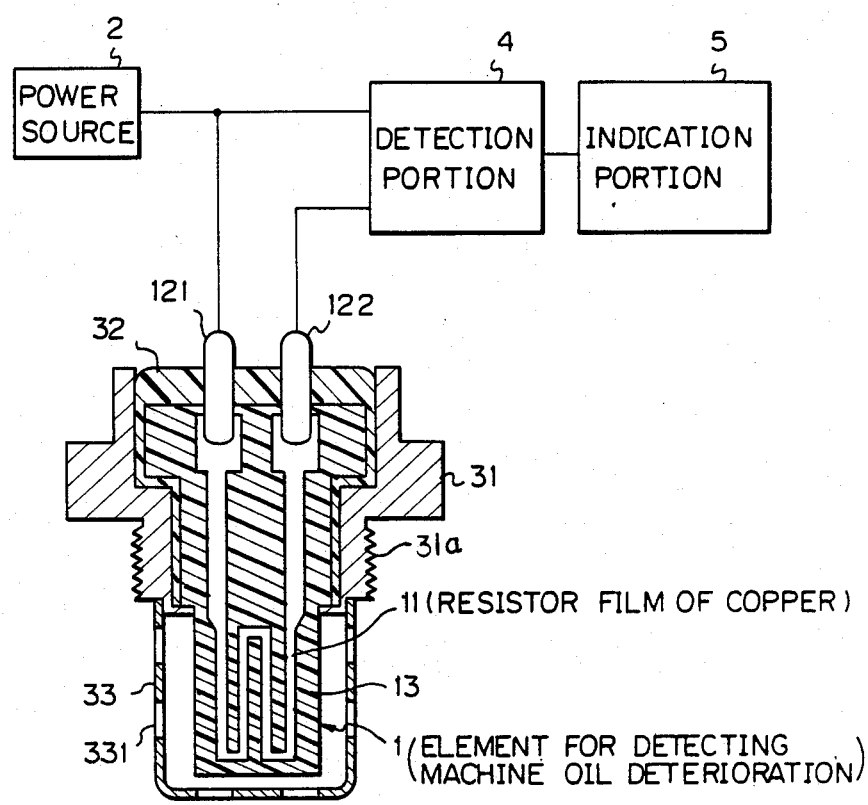
FIG. 1 shows a machine oil deterioration detection apparatus according to an embodiment of the present invention.
Figure 2:
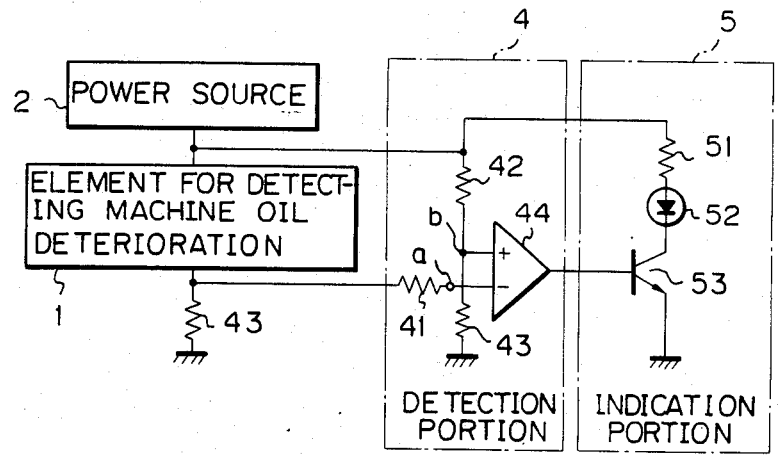
FIG. 2 is a block diagram of an arrangement of the detection and indication portions in the apparatus shown in FIG. 1.
Figure 3:
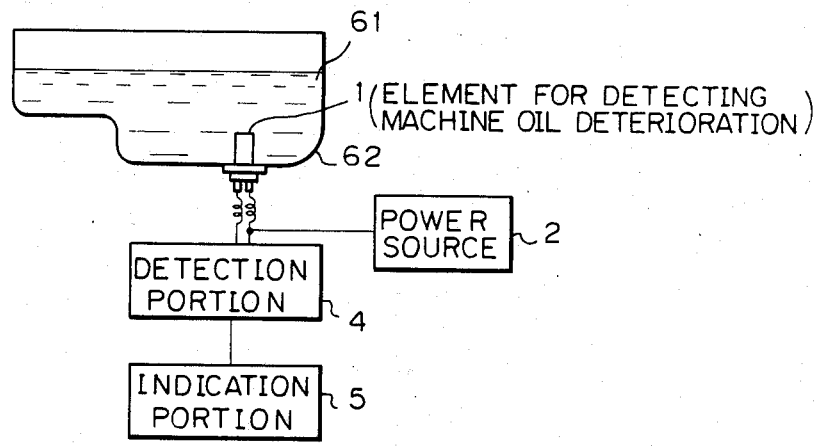
FIG. 3 shows a mounting state on an oil pan of the apparatus of FIG. 1.

Machine Oil Deterioration Detection Element, Deterioration Detection Portion, and Deterioration Indication Portion:

FIGS. 1 to 3 show a machine oil deterioration detection apparatus, according to an embodiment of the present invention, which is mounted on a bottom portion of an oil pan 62 of a vehicle. In the apparatus shown in FIG. 1, an element 1 for detecting machine oil deterioration comprises a substrate 13 and a metal resistor 11. The substrate 13 as a holding member is an insulating member such as alumina, glass, polyimide or the like, and the copper thin film resistor 11 is formed thereon by vacuum deposition, sputtering, ion-plating, plating or the like. A method of manufacturing the element 1 will be described hereinafter.

In the manufacture of the element 1, copper is deposited on an alumina substrate over an area of 50 mm$^2$ and to a thickness of 1.0 mm by a vacuum deposition apparatus. A resist is coated on the resultant structure, which is then prebaked. Thereafter, the resultant structure is exposed by using a photomask having a pattern indicated by reference numeral 11 in FIG. 1, and is developed and rinsed. The structure is then post-baked, and etched by a ferric chloride solution. The resist is then removed by a remover, and the resultant structure cut into a shape indicated by reference numeral 1 in FIG. 1, thus completing the resistor 11. The resistance of the element 1 is adjusted by the film thickness and pattern width and length to be about 1 to 50 Ω. The resistor 11 is made of a metal such as iron, copper, aluminum, brass, zinc or the like.

The element 1 is strongly adhered to a housing 31 by an adhesive 32, such as an epoxy resin, and a threaded portion 31a for fixing the element 1 to the oil pan 62 is formed on the housing 31. The element 1 is provided with lead electrodes 121 and 122 for connecting the resistor 11 to a detection portion 4. In FIG. 1, most parts of the element 1 are illustrated in cross-section. However, the metal resistor 11 and the lead electrodes 121 and 122 are illustrated in elevation. A protective cover 33 with a small hole 331 for protecting the element 1 from damage is provided at a distal end of the housing 31.

FIG. 2 shows the detection and indication portions in the apparatus shown in FIG. 1. In the apparatus shown in FIG. 2, when the resistance of the element 1 is increased in accordance with deterioration of the oil, a potential at point a is decreased. When the potentials at points a and b are inverted, i.e., when the potential at point a becomes lower than that at point b, the output from a comparator 44 goes HIGH, and a voltage is supplied to the base of a transistor 53. A current then flows between the collector and the emitter of the transistor 53 and a light-emitting diode 52 is illuminated, thus signaling the need for replacement of the oil. Although a DC circuit is shown in the figure, an AC voltage can be applied to the detection portion.

Material to be Used and Characteristics of Apparatus using the Material:

The apparatus shown in FIG. 1 will be described by way of Examples with reference to FIGS. 4 to 7 and Table 1 below.

TABLE 1

Figure 4:
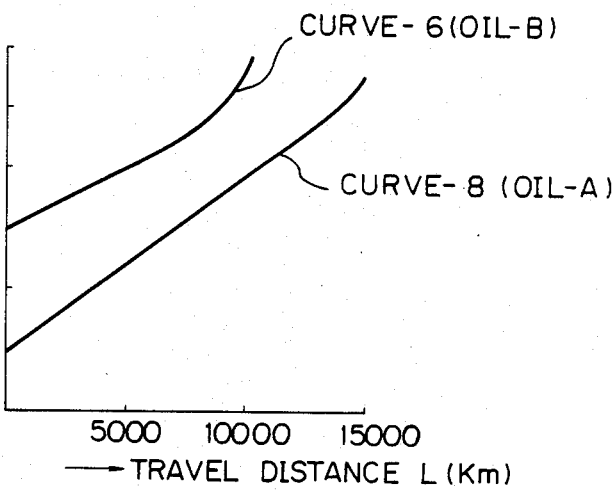
FIG. 4 is a graph showing a total acid number (value) of a machine oil measured by the oil deterioration detection element.
Figure 5:
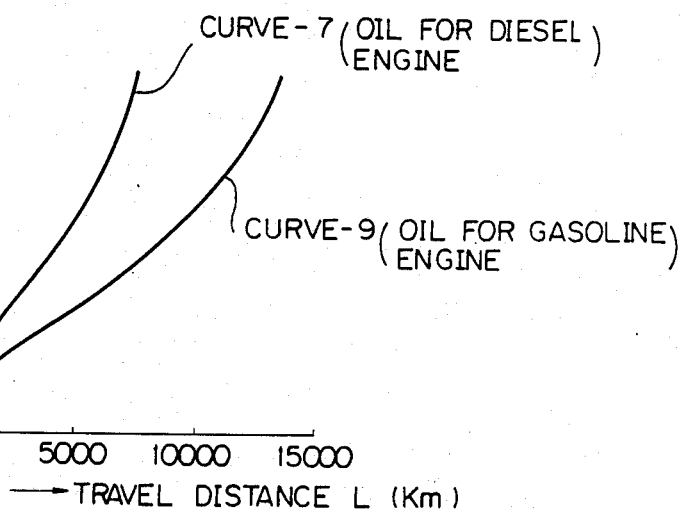
FIGS. 5, 6, and 7 are graphs showing resistance characteristics of the oil deterioration detection element.
Figure 6:
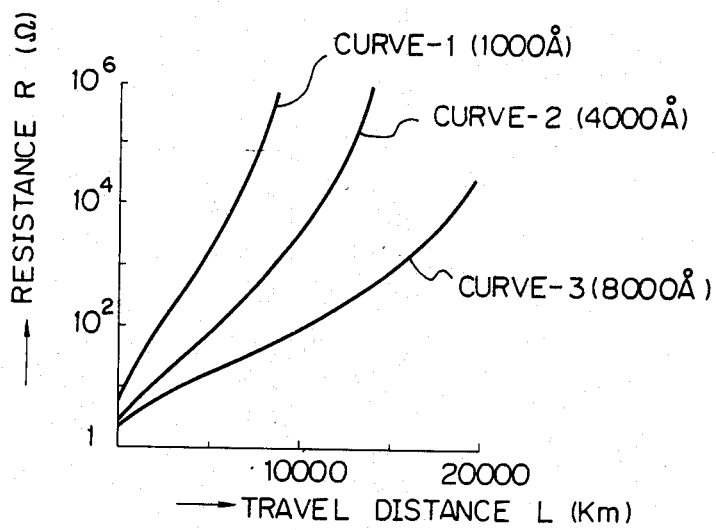
Figure 7:
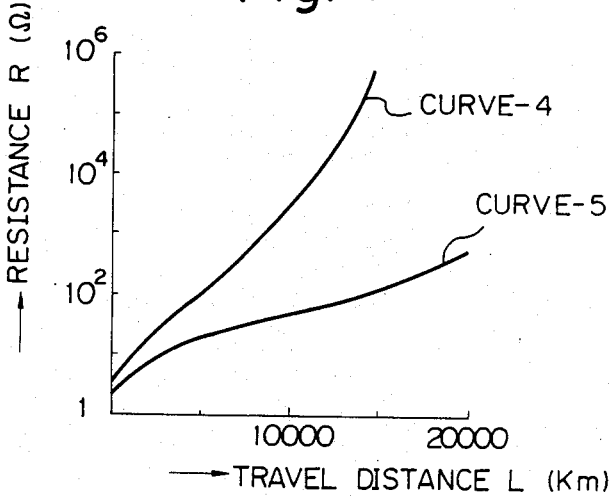

| Drawings | Curve Number | Film Thickness | Film Forming Method | Oil |
|---|---|---|---|---|
| FIG. 6 | CURVE-1 | 1,000Å | Vacuum Deposition | OIL-A |
| FIG. 6 | CURVE-2 | 4,000Å | Vacuum Deposition | OIL-A |
| FIG. 6 | CURVE-3 | 8,000Å | Vacuum Deposition | OIL-A |
| FIG. 7 | CURVE-4 | 1,000Å | Sputtering | OIL-A |
| FIG. 7 | CURVE-5 | 4,000Å | Sputtering | OIL-A |
| FIG. 4 | CURVE-6 | 4,000Å | Vacuum Deposition | OIL-B |
| FIG. 5 | CURVE-7 | 4,000Å | Vacuum Deposition | OIL-B |
| FIG. 4 | CURVE-8 | 4,000Å | Vacuum Deposition | OIL-A |
| FIG. 5 | CURVE-9 | 4,000Å | Vacuum Deposition | OIL-A |

An oil A (OIL-A) "Castle Clean Super 10W-30", a trade name, and an oil B (OIL-B) "Castle Dieselux 10W-30", a trade name, were used as oils for immersion.

Oil detection elements shown in Table 1 were manufactured in accordance with a method described in the apparatus of FIG. 1, and a durability test was conducted using a vehicle "Crown" manufactured by TOYOTA MOTOR CORP. The oils A and B were used as the oils, and a gasoline engine "1G-EU" and a diesel engine "2L-T" were used. FIGS. 5, 6, and 7 are graphs showing the relationship between a travel distance (L) and a resistance (R) obtained from the durability test.

In the durability test, 20 cc of the oil were sampled every 2,000 km, and a total acid number (mgKOH/g) of the sampled oil was measured in accordance with JIS-K-2501. The results are shown in FIG. 4. In the figure, CURVE-6 corresponds to "Dieselux" and CURVE-8 corresponds to "Clean Super." As can be seen from FIG. 4, the total acid number is proportional to the travel distance (L). The travel distance at the total acid number 4 is 10,000 km for the gasoline engine, as indicated by CURVE-8, and is 5,000 km for the diesel engine, as indicated by CURVE-6. These values coincide with the oil replacement limits recommended by the oil company and the vehicle manufacturer.

FIG. 5 is a graph showing the relationship between the travel distance (L) and the resistance (R) of the detection element which was mounted in the same vehicle at the same time as the data in FIG. 4 was obtained.

As is apparent from FIG. 5, CURVE-7 of the resistance of the element dipped in the diesel engine oil and CURVE-9 of the element dipped in the gasoline engine oil correspond to FIG. 4. At the total acid number 4, i.e., at the travel distance of 5,000 km, as indicated by CURVE-6 and 10,000 km, as indicated by CURVE-8, CURVE-7 and CURVE-9 exhibit a resistance of about $5 \times 10^3 \, \Omega$.

In other words, in the apparatus shown in FIG. 2, when a threshold value of the detection portion is set at $5 \times 10^3 \, \Omega$, the oil deterioration indication portion is operated at 5,000 km in the diesel engine, and at 10,000 km in the gasoline engine, thus signalling the need for oil replacement to a user.

FIG. 6 is a graph showing the influence of the film thickness. When the film is too thin, as indicated by CURVE-1, the resistance becomes infinite before the oil replacement limit is reached, and the element cannot be used for detection of the state of the oil deterioration.

FIG. 7 is a graph of the results of a durability test of an element comprising a metal resistor formed by a parallel-plate magnetron sputtering apparatus. As compared with FIG. 6, the change in the resistance of the sputtered film is smaller than that of the deposited film.

Copper as Thin Film Resistor Material:

The reason why the present inventors selected copper as the optimum thin film resistor material will be explained.

Figure 8:
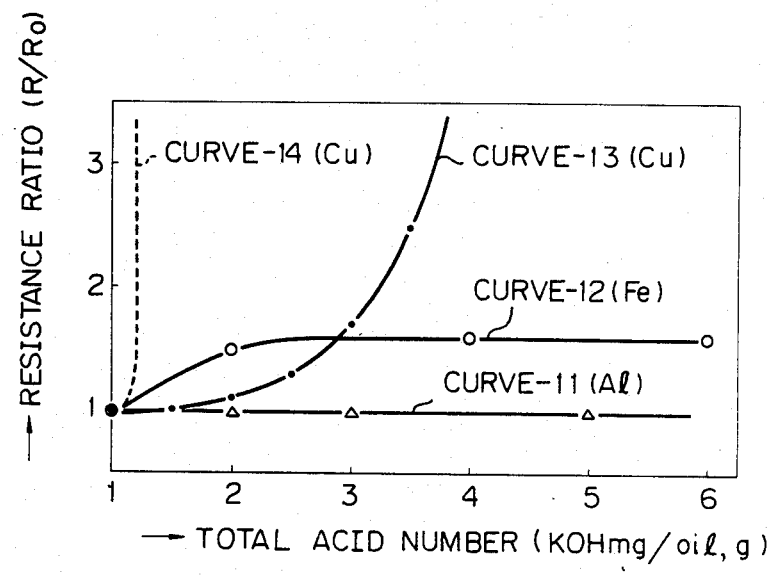
FIG. 8 is a graph showing a change in the resistance of the oil deterioration detection element.

FIG. 8 shows the results of a test in which metal thin film resistors made of copper, iron, and aluminum were dipped in heated oil and the change in resistance was examined. In FIG. 8, the abscissa indicates a change in the total acid number, and the ordinate indicates a change in resistance R after the element is dipped in the oil, in comparison with a prior resistance $R_0$. The experimental conditions are shown in Table 2 below.

TABLE 2

| Curve Number | Material | Film Thickness | Film Forming Method | Oil Temperature |
|---|---|---|---|---|
| CURVE-11 | Al | 1,000Å | Vacuum Deposition | 165° C. |
| CURVE-12 | Fe | 15,000Å | Vacuum Deposition | 165° C. |
| CURVE-13 | Cu | 6,000Å | Vacuum Deposition | 100° C. to 130° C. |
| CURVE-14 | Cu | 6,000Å | Vacuum Deposition | 165° C. |

The above-mentioned "Castle Clean Super 10W-30" was used as the oil.

Referring to FIG. 8, the resistance of the aluminum film is only slightly changed. This is because an oxidation film forms on the surface of the aluminum (Al) film in air, and this film prevents a chemical reaction between the aluminum film and the oil.

Although the resistance of the iron film (Fe) is changed at the beginning of oxidation, the resistance is no longer changed after the total acid number becomes 2 or more. This phenomenon was explained when the present inventors observed the surface of the iron (Fe) film, and found that a passive film of a carbonyl group had formed on the surface of the iron film to a thickness of several tens to several hundreds of angstroms.

The copper film begins to corrode irrespective of the total acid number when the oil temperature reaches 165° C., and the resistance thereof is thus increased. However, within the temperature range of 100° C. to 130° C., a change in resistance can be obtained in accordance with the total acid number. Note that since a temperature of the engine oil in the oil pan rarely exceeds 130° C. even in summer time, the thin film resistor made of copper is most preferable.

Figure 9:
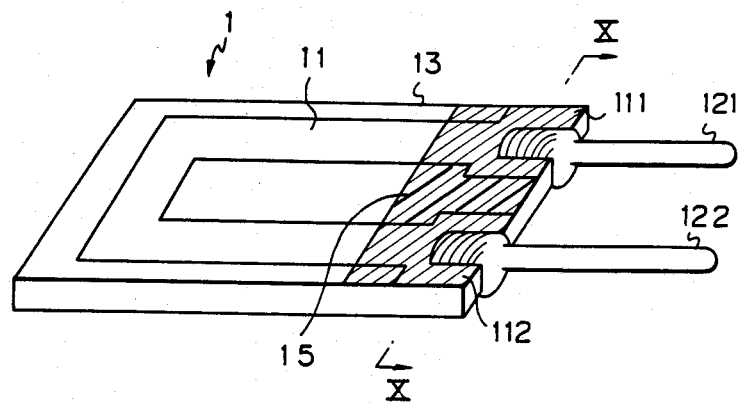
Figure 10:
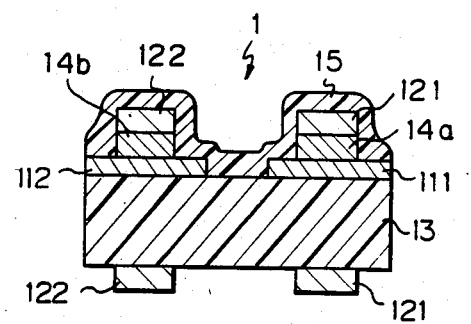

Embodiment shown in FIGS. 9 and 10:

Another embodiment of the present invention will be described hereinafter.

FIGS. 9 and 10 show an oil deterioration detection element 1 comprising an insulating substrate 13 as an example of a holding member of the present invention, a metal thin film resistor 11 formed thereon, lead electrodes 121 and 122 connected to the resistor 11, and an insulating film 15 formed on a connecting portion of the resistor 11 and the electrodes 121 and 122. A method for manufacturing the oil deterioration detection element 1 will be described hereinafter.

In this manufacturing method, copper is deposited on one surface of the insulating substrate 13 made of alumina or a glass plate having a thickness of about 1 mm to a thickness of about 6,000 Å by a vacuum deposition method or a sputtering method. A resist is then coated on the structure, and the structure is prebaked. Thereafter, the structure is exposed by using a photomask having a U-shaped pattern, as shown in FIG. 1, and is developed and rinsed. The resultant structure is then postbaked and etched by a ferric chloride solution, and the resist removed by a remover. Then, the insulating substrate 13 is cut into the shape shown in FIG. 1, to a size of 4 mm×25 mm. The lead electrodes 121 and 122 are made of stainless steel and are connected through connecting portions 14a and 14b made of solder onto lead portions 111 and 112 at two ends of the metal thin film resistor 11 made of copper and formed on the insulating substrate 13 in the above manner. An insulating film 15, made of a material such as $SiO_2$ is formed on the lead portions 111 and 112 and the lead electrodes 121 and 122 to a thickness of about 2 $\mu$m by sputtering, thus completing the machine oil deterioration detection element 1 according to this embodiment of the present invention.

Mounting Structure of Machine Oil Deterioration Detection Apparatus:

FIGS. 11 and 12 show an example wherein the machine oil deterioration detection element 1 formed in the above manner is mounted on an oil level gauge (dipstick) of a vehicle. The lead electrodes 121 and 122 of the element 1 are respectively inserted in connectors 91 and 92 built into a cylindrical rubber block 9 provided at the bottom end of a metal pipe 10. One end of each of the connectors 91 and 92 is connected to a power source 2 and a detection portion 4, respectively, through lead wires 8. The detection portion 4 is connected to an indication portion 5 for indicating that the oil must be replaced when oil deterioration reaches a certain level.

As shown in FIG. 11, a rubber bushing 6 and a handle 7 are provided at the other end of the metal pipe 10. The user can hold the handle 7 and insert the apparatus into a hole of the oil level gauge. Note that since a gauge scale for measuring an oil level is provided on the insulating substrate 13 or at the distal end side of the metal pipe 10, both the oil deterioration detection and the measurement of the oil level can be performed.

In the machine oil deterioration detection apparatus shown in FIG. 1, a metal thin film resistor is formed on a surface of a holding member, and a connecting portion of the metal thin film resistor and an electrode member is coated with an acid-resistant film. For this reason, the apparatus has a practical mechanical strength, and oil deterioration can be precisely detected, thus improving product reliability.

Since the detection element portion immersed in the oil can be compact in size, less space is needed for mounting the deterioration detection apparatus.

We claim:

1. An apparatus for detecting the degree of deterioration of machine oil, comprising:
   a thin film resistor member made of copper and formed on an electrically insulating holding member and adapted to be immersed in the machine oil, said film resistor member subject to being corroded and the electrical resistance thereof between two ends thereof thereby changed upon exposure to an acid which accumulates in the machine oil, in use, due to deterioration of the machine oil;
   respective electrode members conductively joined at respective junctions to said thin film resistor member said two ends of said thin film resistor member; and
   a resistance variation detection circuit operatively connected to said electrode members for detecting a variation in the magnitude of the electrical resistance of said thin film resistor member as a voltage drop between said two ends upon causing an electrical current to flow along said thin film resistor member.

2. An apparatus according to claim 1, further comprising an indicator device operatively connected to said resistance variation detection circuit, said indicator device being adapted for indicating that the machine oil has deteriorated, when the resistance of said thin film resistor member exceeds a predetermined value.

3. An apparatus according to claim 1, further comprising an acid-resistant coating member coating said junctions between said electrode members and said thin film resistor member.

4. An apparatus according to claim 3, further including:
   an oil level gauge including an elongated sheath member adapted to be mounted with one end thereof immersed in an automotive engine oil pan, and an opposite end exposed, and a dip stick telescopically removably received in said sheath; said holding member being mounted to said sheath in the vicinity of said one end of said sheath.

5. An apparatus according to claim 1, wherein:
   said thin film resistor member has a thickness in the range of 1000 Å–6000 Å.

* * * * *